United States Patent [19]

Squiller et al.

[11] Patent Number: 5,489,704
[45] Date of Patent: Feb. 6, 1996

[54] POLYISOCYANATE/POLYAMINE MIXTURES AND THEIR USE FOR THE PRODUCTION OF POLYUREA COATINGS

[75] Inventors: Edward P. Squiller, Pittsburgh, Pa.; Christian Zweiner, Leverkusen, Germany

[73] Assignees: Bayer Corporation, Pittsburgh, Pa.; Bayer Aktiengesellschaft, Leverkusen, Germany

[21] Appl. No.: 297,357

[22] Filed: Aug. 29, 1994

[51] Int. Cl.⁶ ................................................. C07C 229/00
[52] U.S. Cl. ........................... 560/35; 560/118; 560/125; 560/168; 544/200
[58] Field of Search .............................. 560/35, 118, 125, 560/168; 544/200

[56] References Cited

U.S. PATENT DOCUMENTS

| | | | |
|---|---|---|---|
| 3,420,800 | 1/1969 | Haggis | 528/77 |
| 3,567,692 | 3/1971 | Haggis et al. | 528/77 |
| 5,126,170 | 6/1990 | Zwiener | 528/68 |
| 5,214,086 | 5/1993 | Mormile et al. | 524/237 |
| 5,312,962 | 5/1994 | Schäfer et al. | 560/21 |

*Primary Examiner*—James J. Seidleck
*Assistant Examiner*—R. F. Johnson
*Attorney, Agent, or Firm*—Joseph C. Gil; Thomas W. Roy

[57] ABSTRACT

The present invention relates to an aldimine/aspartate corresponding to the formula

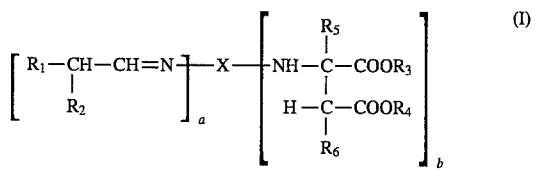

wherein X represents an organic group which has a valency of n and is inert towards isocyanate groups at a temperature of 100° C. or less, $R_1$ and $R_2$ may be the same or different and represent optionally substituted hydrocarbon radicals, or $R_1$ and $R_2$ together with the β-carbon atom form a cycloaliphatic or heterocyclic ring and $R_3$ and $R_4$ may be identical or different and represent organic groups which are inert towards isocyanate groups at a temperature of 100° C. or less, $R_5$ and $R_6$ may be identical or different and represent hydrogen or organic groups which are inert towards isocyanate groups at a temperature of 100° C. or less, and a and b represent integers with a value of 1 to 5, provided that the sum of a and b is 2 to 6.

The present invention also relates to coating compositions containing these aldimine aspartates and polyisocyanates, and to the use of these coating compositions for the production of polyurea coatings.

4 Claims, No Drawings

POLYISOCYANATE/POLYAMINE MIXTURES AND THEIR USE FOR THE PRODUCTION OF POLYUREA COATINGS

BACKGROUND OF THE INVENTION

1. Field of the Invention

The present invention relates to polyisocyanate/polyamine mixtures in which the binder components possess improved compatibility with one another resulting in the production of coatings with improved optical properties, e.g., clarity.

2. Description of the Prior Art

One-component coating compositions which may be cured at room temperature are known and contain fully reacted polyurethanes as the binder. These compositions have the advantage that they are available as fully formulated systems which may be directly applied to suitable substrates without any preliminary steps except for mild stirring. Disadvantages of these systems are that large amounts of organic solvents are needed to reduce the viscosity of fully reacted, i.e., high molecular weight, polyurethanes and the polyurethanes must be essentially linear polyurethanes, which do not possess certain properties, e.g., solvent resistance, which may be obtained from crosslinked polyurethanes.

Two-component coating compositions are also known. These compositions come in two containers. The first contains a polyisocyanate, while the second contains an isocyanate-reactive component, generally a polyol. These systems do not require large amounts of solvent to obtain a suitable processing viscosity and can be used to obtain highly crosslinked coatings which possess properties that surpass those possessed by one-component coatings. However, these systems must be accurately mixed or the properties of the resulting coatings can be substantially affected. In addition, after the components are mixed they have a limited pot life since the components continue to react until an unusable solid is obtained.

Coating compositions which possess the advantages of the known one- and two-component coating compositions without possessing their disadvantages have been disclosed in copending applications, U.S. Ser. Nos. 08/171,281; 08/171,550; 08/171,304; 08/193,978; and 08/194,296. The coating compositions are prepared by blending polyisocyanates with certain aldimines. Even though coatings prepared in accordance with these copending applications possess many desirable properties, further improvements are needed in the appearance of the coatings, i.e., clarity, gloss and distinctness of image (DOI). These properties are directly related to the compatibility between the polyisocyanate and the aldimine.

Copending application, U.S. Ser. No. 08/171,281, discloses that the compatibility with aldimines may be improved by using certain allophanate group-containing polyisocyanates. However, there is still a need to achieve these improvements in compatibility and appearance with other commercially available polyisocyanates. In addition, even though the allophanate group-containing polyisocyanates described in the copending application are compatible with aldimines, they are not initially compatible with all aldimines, i.e., a cloudy solution may initially be formed. It may take 30 minutes or longer before a clear solution is obtained. In those applications in which it is desired to prepare a coating immediately after blending the components of the coating composition, it is necessary to improve the initial compatibility between the allophanate group-containing polyisocyanates and aldimines.

It is an object of the present invention to improve the compatibility, including the initial compatibility between polyisocyanates and aldimines so that the clarity, gloss and DOI of the resulting coatings is also improved. This object may be achieved with coating compositions according to the invention, which in addition to polyisocyanates and aldimines, also contain the polyaspartates described hereinafter.

U.S. Pat. Nos. 3,420,800 and 3,567,692 disclose coating compositions containing polyisocyanates and either aldimines or ketimines. U.S. Pat. No. 5,126,170 discloses coating compositions containing polyisocyanates, polyaspartates and optionally polyols. However, these patents do not teach that the compatibility of polyisocyanates with aldimines can be improved by the use of aldimine/aspartates of the present invention.

U.S. Pat. No. 5,214,086 discloses coating compositions containing polyisocyanates, aldimines, polyols and optionally polyaspartates. The examples of the present invention demonstrate that the coating compositions according to the invention possess superior properties when compared to the four component compositions disclosed by U.S. Pat. No. 5,214,086.

Copending application, U.S. Ser. No. 08/273,551, discloses that the compatibility of polyisocyanates with aldimines can be improved by also incorporating aspartates into the composition.

SUMMARY OF THE INVENTION

The present invention relates to an aldimine/aspartate corresponding to the formula

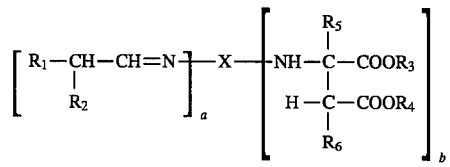

wherein
X represents an organic group which has a valency of n and is inert towards isocyanate groups at a temperature of 100° C. or less, $R_1$ and $R_2$ may be the same or different and represent optionally substituted hydrocarbon radicals, or $R_1$ and $R_2$ together with the β-carbon atom form a cycloaliphatic or heterocyclic ring and $R_3$ and $R_4$ may be identical or different and represent organic groups which are inert towards isocyanate groups at a temperature of 100° C. or less and $R_5$ and $R_6$ may be identical or different and represent hydrogen or organic groups which are inert towards isocyanate groups at a temperature of 100° C. or less, and a and b represent integers with a value of 1 to 5, provided that the sum of a and b is 2 to 6.

The present invention also relates to a coating composition
containing
a) a polyisocyanate component and
b) an isocyanate-reactive component containing an aldimine/aspartate corresponding to the formula

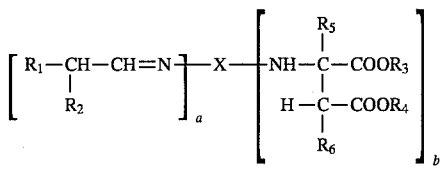

c) 0 to 75% by weight, based on the weight of component b), c) and d), of an aldimine corresponding to the formula $$X\!\!+\!\!N\!=\!CHCH(R_1)(R_2)]_n$$

and d) 0 to 50% by weight, based on the weight of components b), c) and d), of an aspartate corresponding to the formula

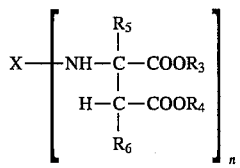

wherein

X, $R_1$, $R_2$, $R_3$, $R_4$, $R_5$, $R_6$, a and b are defined as set forth above and n represents an integer with a value of 2 to 6, and wherein polyisocyanate a) and isocyanate-reactive component b) are present in an amount sufficient to provide an equivalent ratio of isocyanate groups to aldimine groups and aspartate groups of 0.5:1 to 20:1.

The present invention further relates to a coating composition containing a) a polyisocyanate component, b) 15 to 100% by weight, based on the weight of components b), c) and d), of an aldimine/aspartate component corresponding to the formula

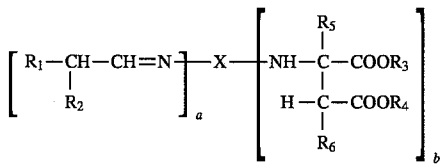

c) 0 to 75% by weight, based on the weight of component b), c) and d), of an aldimine corresponding to the formula $$X\!\!+\!\!N\!=\!CHCH(R_1)(R_2)]_n$$

and d) 0 to 50% by weight, based on the weight of components b), c) and d), of an aspartate corresponding to the formula

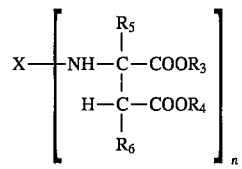

wherein X, $R_1$, $R_2$, $R_3$, $R_4$, $R_5$, $R_6$, a, b and n are defined as set forth above, wherein components a), b), c) and d) are present in an amount sufficient to provide an equivalent ratio of isocyanate groups to aldimine groups and aspartate groups of 0.5:1 to 20:1 and wherein components b) and optionally d) are present in an amount sufficient to form a clear solution within 60 minutes of mixing components a), b), c) and d).

Finally, the present invention relates to a polyurea coating prepared from these coating compositions.

DETAILED DESCRIPTION OF THE INVENTION

Examples of suitable polyisocyanates which may be used as the polyisocyanate component in accordance with the present invention include monomeric diisocyanates, preferably NCO prepolymers and more preferably polyisocyanate adducts. Suitable monomeric diisocyanates may be represented by the formula $$R(NCO)_2$$

in which R represents an organic group obtained by removing the isocyanate groups from an organic diisocyanate having a molecular weight of about 112 to 1,000, preferably about 140 to 400. Diisocyanates preferred for the process according to the invention are those represented by the above formula in which R represents a divalent aliphatic hydrocarbon group having 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of the suitable organic diisocyanates include 1,4-tetramethylene diisocyanate, 1,6-hexamethylene diisocyanate, 2,2,4-trimethyl- 1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethylcyclohexane (isophorone diisocyanate or IPDI), bis-(4-isocyanatocyclohexyl)-methane, 2,4'-dicyclohexyl-methane diisocyanate, 1,3- and 1,4-bis-(isocyanatomethyl)-cyclohexane, bis-(4-isocyanato-3-methylcyclohexyl)-methane, α,α, α',α'-tetramethyl-1,3- and/or -1,4-xylylene diisocyanate, 1-isocyanato-1-methyl-4(3)-isocyanatomethyl cyclohexane, 2,4- and/or 2,6-hexahydrotoluylene diisocyanate, 1,3- and/or 1,4-phenylene diisocyanate, 2,4- and/or 2,6-toluylene diisocyanate, 2,4- and/or 4,4'-diphenyl-methane diisocyanate, 1,5-diisocyanato naphthalene and mixtures thereof. Aromatic polyisocyanates containing 3 or more isocyanate groups such as 4,4',4"-triphenylmethane diisocyanate and polyphenyl polymethylene polyisocyanates obtained by phosgenating aniline/formaldehyde condensates may also be used.

In accordance with the present invention the polyisocyanate component is preferably in the form of an NCO prepolymer or a polyisocyanate adduct, more preferably a polyisocyanate adduct. Suitable polyisocyanate adducts are those containing isocyanurate, uretdione, biuret, urethane, allophanate, carbodiimide and/or oxadiazinetrione groups. The polyisocyanates adducts have an average functionality of 2 to 6 and an NCO content of 5 to 30% by weight.

1) Isocyanurate group-containing polyisocyanates which may be prepared as set forth in DE-PS 2,616,416, EP-OS 3,765, EP-OS 10,589, EP-OS 47,452, U.S. Pat. Nos. 4,288,586 and 4,324,879. The isocyanato-isocyanurates generally have an average NCO functionality of 3 to 3.5 and an NCO content of 5 to 30%, preferably 10 to 25% and most preferably 15 to 25% by weight.

2) Uretdione diisocyanates which may be prepared by oligomerizing a portion of the isocyanate groups of a diisocyanate in the presence of a trialkyl phosphine catalyst and which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,906,126; 3,903,127; 4,051,165; 4,147,714; or 4,220,749 by using co-reactants such as water, tertiary alcohols, primary and secondary monoamines, and primary and/or secondary diamines. These polyisocyanates preferably have an NCO content of 18 to 22% by weight and an average NCO functionality of 3 to 3.5.

4) Urethane group-containing polyisocyanates which may be prepared in accordance with the process disclosed in U.S. Pat. No. 3,183,112 by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof. The urethane group-containing polyisocyanates have a most preferred NCO content of 12 to 20% by weight and an (average) NCO functionality of 2.5 to 3.

5) Allophanate group-containing polyisocyanates which may be prepared according to the processes disclosed in U.S. Pat. Nos. 3,769,318, 4,160,080 and 4,177,342. The allophanate group-containing polyisocyanates have a most preferred NCO content of 12 to 21% by weight and an (average) NCO functionality of 2 to 4.5.

6) Isocyanurate and allophanate group-containing polyisocyanates which may be prepared in accordance with the processes set forth in U.S. Pat. Nos. 5,124,427, 5,208,334 and 5,235,018, the disclosures of which are herein incorporated by reference, preferably polyisocyanates containing these groups in a ratio of monoisocyanurate groups to monoallophanate groups of about 10:1 to 1:10, preferably about 5:1 to 1:7.

7) Carbodiimide group-containing polyisocyanates which may be prepared by oligomerizing di- or polyisocyanates in the presence of known carbodiimidization catalysts as described in DE-PS 1,092,007, U.S. Pat. No. 3,152,162 and DE-OS 2,504,400, 2,537,685 and 2,552,350.

8) Polyisocyanates containing oxadiazinetrione groups and containing the reaction product of two moles of a diisocyanate and one mole of carbon dioxide.

Preferred polyisocyanate adducts are the polyisocyanates containing isocyanurate groups, biuret groups or mixtures of isocyanurate and allophanate groups.

The NCO prepolymers, which may also be used as the polyisocyanate component in accordance with the present invention, are prepared from the previously described monomeric polyisocyanates or polyisocyanate adducts, preferably monomeric diisocyanates, and organic compounds containing at least two isocyanate-reactive groups, preferably at least two hydroxy groups. These organic compounds include high molecular weight compounds having molecular weights of 400 to about 6,000, preferably 800 to about 3,000, and optionally low molecular weight compounds with molecular weights below 400. The molecular weights are number average molecular weights ($M_n$) and are determined by end group analysis (OH number). Products obtained by reacting polyisocyanates exclusively with low molecular weight compounds are polyisocyanates adducts containing urethane groups and are not considered to be NCO prepolymers.

Examples of the high molecular weight compounds are polyester polyols, polyether polyols, polyhydroxy polycarbonates, polyhydroxy polyacetals, polyhydroxy polyacrylates, polyhydroxy polyester amides and polyhydroxy polythioethers. The polyester polyols, polyether polyols and polyhydroxy polycarbonates are preferred. Further details concerning the low molecular weight compounds and the starting materials and methods for preparing the high molecular weight polyhydroxy compounds are disclosed in U.S. Pat. No. 4,701,480, herein incorporated by reference.

These NCO prepolymers generally have an isocyanate content of about 0.5 to 30% by weight, preferably about 1 to 20% by weight, and are prepared in known manner by the reaction of the above mentioned starting materials at an NCO/OH equivalent ratio of about 1.05:1 to 10:1 preferably about 1.1:1 to 3:1. This reaction may take place in a suitable solvent which may optionally be removed by distillation after the reaction along with any unreacted volatile starting polyisocyanates still present. In accordance with the present invention NCO prepolymers also include NCO semi-prepolymers which contain unreacted starting polyisocyanates in addition to the urethane group-containing prepolymers.

Suitable aldimine/aspartates for use as component b) include those corresponding to the formula

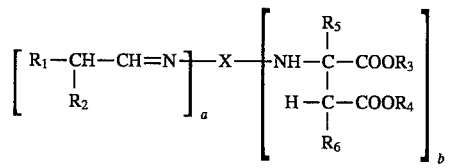

wherein

X represents an organic group which has a valency of n and is inert towards isocyanate groups at a temperature of 100° C. or less, preferably a hydrocarbon group obtained by the removal of the amino groups from an aliphatic, araliphatic or cycloaliphatic polyamine, more preferably a diamine, $R_1$ and $R_2$ may be the same or different and represent optionally substituted hydrocarbon radicals, preferably containing 1 to 10, more preferably 1 to 6, carbon atoms, or $R_1$ and $R_2$ together with the β-carbon atom form a cycloaliphatic or heterocyclic ring, $R_3$ and $R_4$ may be identical or different and represent organic groups which are inert towards isocyanate groups at a temperature of 100° C. or less, preferably methyl or ethyl groups, $R_5$ and $R_6$ may be identical or different and represent hydrogen or organic groups which are inert towards isocyanate groups at a temperature of 100° C. or less, preferably hydrogen, a and b represent integers with a value of 1 to 5, preferably 1 to 3 and more preferably 1, provided that the sum of a and b is 2 to 6, preferably 2 to 4 and more preferably 2, and n equals a+b.

The aldimine/aspartates are prepared by reacting polyamines with aldehydes and optionally substituted maleic or fumaric acid esters. Suitable polyamines are those corresponding to the formula $$X\text{--}(NH_2)_n$$

wherein

X is as previously defined and n represent an integers with a value of 2 to 6, preferably 2 to 4 and more preferably 2.

The polyamines include high molecular weight amines having molecular weights of 400 to about 10,000, preferably 800 to about 6,000, and low molecular weight amines having molecular weights below 400. The molecular weights are number average molecular weights ($M_n$) and are determined by end group analysis (NH number). Examples of these polyamines are those wherein the amino groups are attached to aliphatic, cycloaliphatic, araliphatic and/or aromatic carbon atoms.

Suitable low molecular polyamine starting compounds include ethylene diamine, 1,2- and 1,3-propane diamine, 2-methyl-1,2-propane diamine, 2,2-dimethyl-1,3-propane diamine, 1,3- and 1,4-butane diamine, 1,3- and 1,5-pentane diamine, 2-methyl-1,5-pentane diamine, 1,6-hexane diamine, 2,5-dimethyl-2,5-hexane diamine, 2,2,4- and/or 2,4,4-trimethyl-1,6-hexane diamine, 1,7-heptane diamine, 1,8-octane diamine, 1,9-nonane diamine, 1,10-decane diamine, 1,11-undecane diamine, 1,12-dodecane diamine, 1-amino-3-aminomethyl-3,5,5-trimethyl cyclohexane, 2,4- and/or 2,6-hexahydrotoluylene diamine, 2,4'- and/or 4,4'-diamino-dicyclohexylmethane, 3,3'-dialkyl-4,4'-diamino-dicyclohexyl methanes (such as 3,3'-dimethyl-4,4'-diamino-dicyclohexyl methane and 3,3'-diethyl-4,4'-diamino-dicyclohexyl methane), 1,3- and/or 1,4-cyclohexane diamine, 1,3-bis(methylamino)-cyclohexane, 1,8-p-menthane diamine, hydrazine, hydrazides of semicarbazido carboxylic acids, bis-hydrazides, bis-semicarbazides, phenylene diamine, 2,4- and 2,6-toluylene diamine, 2,3- and 3,4-toluylene diamine, 2,4'- and/or 4,4'-diaminodiphenyl methane, higher functional polyphenylene polymethylene polyamines obtained by the aniline/formaldehyde condensation reaction, N,N,N-tris-(2-aminoethyl)-amine, guanidine, melamine, N-(2-aminoethyl)-1,3-propane diamine, 3,3'-diamino-benzidine, polyoxypropylene amines, polyoxyethylene amines, 2,4-bis-(4'-aminobenzyl)-aniline and mixtures thereof.

Preferred polyamines are 1-amino-3-aminomethyl-3,5,5-trimethylcyclohexane (isophorone diamine or IPDA), bis-(4-aminocyclo-hexyl)-methane, bis-(4-amino-3-methylcyclohexyl)-methane, 1,6-diamino-hexane, 2-methyl pentamethylene diamine and ethylene diamine.

Suitable high molecular weight polyamines correspond to the polyhydroxyl compounds used to prepare the NCO prepolymers with the exception that the terminal hydroxy groups are converted to amino groups, either by amination or by reacting the hydroxy groups with a diisocyanate and subsequently hydrolyzing the terminal isocyanate group to an amino group. Preferred high molecular weight polyamines are amine-terminated polyethers such as the Jeffamine resins available from Texaco.

Suitable optionally substituted maleic or fumaric acid esters for use in the preparation of the aldimine/aspartates are those corresponding to the formula $$\text{--}R_3OOC\text{--}CR_5\text{=}CR_6\text{--}COOR_4\text{--}$$

wherein $R_5$, $R_6$, $R_3$ and $R_4$ are as previously defined. Examples include the dimethyl, diethyl and di-n-butyl esters of maleic acid and fumaric acid and the corresponding maleic or fumaric acid esters substituted by methyl in the 2- and/or 3-position.

Suitable aldehydes for use in preparing the aldimine/aspartates are those corresponding to the formula $$O\text{=}CHCH(R_1)(R_2)$$

wherein $R_1$ and $R_2$ are as previously defined. Examples include isobutyraldehyde, 2-ethyl hexanal, 2-methyl butyraldehyde, 2-ethyl butyraldehyde, 2-methyl valeraldehyde, 2,3-dimethyl valeraldehyde, 2-methyl undecanal and cyclohexane carboxyaldehyde.

The preparation of aldimine/aspartates b) takes place in known manner by reacting the polyamines with the aldehydes and the maleic or fumaric acid esters, either successively or in admixture, at a temperature of 0° to 100° C. Excess starting materials and the water which is produced by the aldehyde/amine condensation reaction may be removed by distillation after the reaction. The reaction may be carried out solvent-free or in the presence of suitable solvents such as methanol, ethanol, propanol, dioxane and mixtures of such solvents.

Preferably, the reaction is conducted in two steps by first reacting a portion of the amino groups with the maleic or fumaric acid esters and then reacting the remaining amino groups with an excess of aldehyde. The excess aldehyde and generated water is then removed by distillation.

Suitable aldimines for use as component c) include those prepared from the aldehydes and polyamines previously set forth as suitable for preparing the aldimine/aspartates.

The aldimines may be prepared in known manner by reacting the polyamines with the aldehydes either in stoichiometric amounts or with an excess of aldehyde. The excess aldehyde and the water which is produced can be removed by distillation. The aldimines may be prepared in the presence of suitable solvents such as those previously set forth. The solvents may also be removed by distillation after completion of the reaction.

Suitable aspartates for use as component d) include those prepared from the optionally substituted maleic or fumaric acid esters and polyamines previously set forth as suitable for preparing the aldimine/aspartates. The aspartates are prepared in known manner by reacting the polyamines with the optionally substituted maleic or fumaric acid esters under the conditions set forth for preparing the aldimine/aspartates.

It is also possible to prepare mixtures predominantly containing aldimine/aspartate b) and aldimine c) or aldimine/aspartate b) and aspartate d) without the need to separately prepare and blend these components. For example, mixtures of components b) and c) (which will also contain a portion of component d)) may be prepared by reacting less than 50% of the amino groups of a diamine with a maleic or fumaric acid ester and then reacting the remainder of the amino groups with an aldehyde. The percentage of component c) in the mixture can be theoretically calculated from percentage of amino groups which can react with the maleic or fumaric acid ester. The smaller the percentage of amino groups which react with maleic or fumaric acid ester, the greater the percentage of component c) which will be present in the mixture in combination with the aldimine/aspartates.

Similarly, mixtures of components b) and d) (which will also contain a portion of component c)) may be prepared by reacting more than 50% of the amino groups with the maleic or fumaric acid ester and then reacting the remainder of the amino groups with an aldehyde. The greater the percentage of amino groups which react with maleic or fumaric acid ester, the greater the percentage of component d) which will be present in the mixture in combination with the aldimine aspartates.

Mixtures of components b) and c); components b) and d); or components b), c) and d) can also be prepared by separately preparing these components and then blending them or, e.g., by adding separately prepared components to mixtures of components b) and c) or components b) and d) prepared as described above. In this way any desired mixtures may be prepared.

The binders present in the coating compositions according to the invention contain polyisocyanate component a), aldimine/aspartate component b), aldimine component c) and aspartate component d). The coating compositions preferably may also contain polyols, i.e., compounds containing hydroxyl groups. However, this is a less preferred embodiment of the present invention since the presence of polyols reduces the pot life of the coating compositions.

Components a), b), c) and d) are used in amounts sufficient to provide an equivalent ratio of isocyanate groups to aldimine groups and aspartate groups of 0.5:1 to 20:1, preferably 0.8:1 to 3:1 and more preferably 1:1 to 2:1. Upon mixing components a), b), c) and d) should form a clear solution within 60 minutes, preferably within 30 minutes, more preferably within 5 minutes and most preferably upon the mixing of the components.

Aldimine c) is not compatible with most polyisocyanates, i.e., mixtures of these components are cloudy and result in hazy coatings. However, aldimine/aspartate b) is compatible with most polyisocyanates. Therefore, it is possible to prepare coating compositions in which the components are compatible by combining polyisocyanate component a) with aldimine groups in the form of component b).

It is also possible for component b) to compatibilize additional amounts of aldimine groups, in the form of component c), with polyisocyanate component a). If a particular mixture of aldimine/aspartate b) and aldimine c) is not compatible with a particular polyisocyanate a), then the amount of component b) must be increased or the amount of component c) must be decreased. Another possibility for increasing the compatibility of particular mixture of components b) and c) with polyisocyanate a) is to add a portion of aspartate d) to the mixture since aspartate d) is compatible with most polyisocyanates.

The amount of components b) and optionally d) which are necessary to compatibilize a particular amount of component c) with polyisocyanate component a) to obtain a clear solution is dependent upon the particular compounds which are used as components a), b), c) and d). This amount can be determined in a simple preliminary test by preparing compositions containing polyisocyanate a) and aldimine c), varying the amounts of aldimine/aspartate b) and optionally aspartate d) and then determining the minimum amount components b) and optionally d) which are necessary to obtain a clear solution. Alternatively, although less preferred, the amount of components b) and optionally d) can be determined by continually adding amounts of these components to a cloudy mixture of components a) and c) until the solution becomes clear.

Generally, the compositions according to the invention contain 15 to 100%, preferably 20 to 80% and more preferably 30 to 70%, by weight of component b); 0 to 75%, preferably 5 to 75% and more preferably 20 to 70%, by weight of component c); and 0 to 50%, preferably 0 to 40 and more preferably 0 to 30%, by weight of component d).

The binders to be used according to the invention are prepared by mixing all of the individual components together or by premixing two or more of the components before adding the other components. However, it is preferable to mix the isocyanate-reactive components together and then to blend the resulting mixture with polyisocyanate component a).

Preparation of the binders is carried out solvent-free or in the presence of the solvents conventionally used in polyurethane or polyurea coatings. It is an advantage of the process according to the invention that the quantity of solvent used may be greatly reduced when compared with that required in conventional two-component systems based on polyisocyanates and polyols.

Examples of suitable solvents include xylene, butyl acetate, methyl isobutyl ketone, methoxypropyl acetate, N-methyl pyrrolidone, Solvesso solvent, petroleum hydrocarbons and mixtures of such solvents.

In the coating compositions to be used for the process according to the invention, the ratio by weight of the total quantity of binder components a), b), c) and d) to the quantity of solvent is about 40:60 to 100:0, preferably about 60:40 to 100:0.

In addition to binder components a), b), c) and d), the coating compositions may also contain the known additives from coatings technology, such as fillers, pigments, softeners, high-boiling liquids, catalysts, UV stabilizers, antioxidants, microbiocides, algicides, dehydrators, thixotropic agents, wetting agents, flow enhancers, matting agents, anti-slip agents, aerators and extenders. Coating compositions containing pigments and/or fillers are especially suitable for the present invention due to the difficulty of removing all of the moisture from these additives.

It is also possible to incorporate other additives which increase the pot life of compositions containing polyisocyanates and aldimines, such as the tin compounds disclosed in copending application, U.S. Ser. No. 08/171,304, and in U.S. Pat. No. 5,243,012, the disclosures of which are herein incorporated by reference; or the zeolites disclosed in copending applications, U.S. Ser. Nos. 08/193,978 and 08/194,296, the disclosures of which are herein incorporated by reference.

The additives are chosen based on the requirements of the particular application and their compatibility with components a), b), c) and d). The coating compositions may be applied to the substrate to be coated by conventional methods such as painting, rolling, pouring or spraying.

The coating compositions according to the invention have good storage stability and provide coatings which have relatively fast dry times. The coatings are also characterized by high hardness, elasticity, very good resistance to chemicals, high gloss, good weather resistance, good environmental etch resistance and good pigmenting qualities.

The invention is further illustrated, but is not intended to be limited by the following examples in which all parts and percentages are by weight unless otherwise specified.

EXAMPLES

The following starting materials were used in the examples:

Polyisocyanate 1

An isocyanurate group-containing polyisocyanate prepared from 1,6-hexamethylene diisocyanate and having an isocyanate content of 21.6%, a content of monomeric diisocyanate of <0.2% and a viscosity at 20° C. of 3000 mPa.s (available from Miles Inc. as Desmodur N 3300).

Polisocyanate 2

A biuret group-containing polyisocyanate prepared from 1,6-hexamethylene diisocyanate and having an isocyanate content of about 23%, a content of monomeric diisocyanate of <0.7% and a viscosity at 25° C. of 1300–2200 mPa.s (available from Miles Inc. as Desmodur N 3200).

Polyisocyanate 3

A polyisocyanate containing isocyanurate groups and allophanate groups was prepared by adding 301.7 parts of hexamethylene diisocyanate and 13.3 parts of 1-butanol to a 500 ml 3-neck flask equipped with a gas bubbler, mechanical stirrer, thermometer and condenser. The stirred mixture was heated for 1 hour at 60° C. while dry nitrogen was bubbled through the reaction mixture. The temperature of the reaction mixture was then raised to 90° C. To the reaction mixture at 90° C. were added 0.214 parts of a 4.4% solution of N,N,N-trimethyl-N-benzyl-ammonium hydroxide in 1-butanol. When the reaction mixture reached an NCO content of 34.8%, the reaction was stopped by adding 0.214 parts of di-(2-ethylhexyl)-phosphate. The excess monomer was removed by thin film evaporation to provide an almost colorless, clear liquid having a viscosity of 630 mPa.s (25° C.), an NCO content of 19.7% and a free monomer (HDI) content of 0.35%. The yield was 48.6%.

Aldimine 1

158.4 of isobutyraldehyde (2.2 mole) were charged at ambient temperature into a three necked 500 ml flask equipped with a mechanical stirrer, thermometer, and an addition funnel. 210 g of 4,4'-diamino-dicyclohexylmethane (1.0 mole) were added dropwise via the addition funnel to the stirred contents of the flask at a rate such that the exotherm of the reaction did not increase the temperature of the reaction mixture above 50° C. During the course of the reaction water was generated as a by-product as evidenced by the gradual change in the appearance of the reaction contents to a milky white mixture. Upon complete addition of the aldehyde, the reaction mixture was heated to maintain a temperature of 50° C. for a period of 1 hour. The water (36 g; 2.0 moles) and excess isobutyraldehyde were removed by azeotropic distillation, followed by a vacuum (ca. 1 torr) stripping step to remove trace quantities of water. The finished product was a clear, almost colorless (<100 APHA) liquid having a viscosity of about 100 mPa.s) 25° C. and an equivalent weight of 159.3 g/eq.

Aspartate 1

210 g of 4,4'-diamino-dicyclohexylmethane (1.0 mole) were added dropwise with stirring to 344 g of maleic acid diethylester (2.0 moles) that were previously charged at ambient temperature to a 1 liter, three necked flask equipped with a stirrer, thermometer and an addition funnel. The amine was added at a rate such that the exotherm did not increase the temperature of the reaction mixture above 50° C. Upon complete addition of the maleic acid diethyl ester, the contents of the reaction flask were maintained at 50° C. for a period of 12 hours. The resulting product was a clear, colorless liquid having a viscosity of about 1400 mPa.s (25° C.) and an equivalent weight of about 276 g/eq.

Preparation of Aldimine/Aspartates According to the Invention

EXAMPLE 1

Aldimine/Aspartates Based on 4,4'-diamino-dicyclohexylmethane.

4,4'-diamino-dicyclohexylmethane (exact charge amounts for all of the reaction components are listed in Table 1) was charged at ambient temperature to a 2 liter, three necked flask equipped with a stirrer, thermometer and an addition funnel. Maleic acid diethylester (DEM) was then added dropwise to the reaction pot with stirring at a rate such that the reaction exotherm did not increase the temperature of the reaction mixture above 50° C. Upon complete addition of the maleic acid diethyl ester, the contents of the reaction flask were maintained at 50° C. for a period of 6 hours. Isobutyraldehyde was then added dropwise to the reaction mixture at a rate such that the reaction exotherm did not increase the temperature above 50° C. During the course of the reaction water was formed as a by-product as evidenced by the reaction mixture turning milky white in appearance. Upon complete addition of the aldehyde, the reaction mixture was heated to maintain a temperature of 50° C. for a period of 1 hour. The water and excess isobutyraldehyde were removed by azeotropic distillation, followed by a vacuum (ca. 1 torr) stripping step to remove trace quantities of water.

TABLE 1

|  | A | B | C | D | E | F |
| --- | --- | --- | --- | --- | --- | --- |
| Amine (grams) | 525 | 420 | 315 | 210 | 158 | 140 |
| DEM (grams) | 172 | 172 | 172 | 172 | 172 | 172 |
| Amine/DEM Mol Ratio | 2.5/1.0 | 2.0/1.0 | 1.5/1.0 | 1.0/1.0 | 0.75/1.0 | 0.67/1.0 |
| Aldehyde (grams) | 288.4 | 216.3 | 144.2 | 72.1 | 36 | 25 |
| Mole of Aldehyde | 4.0 | 3.0 | 2.0 | 1.0 | 0.5 | 0.35 |
| Theo. Ald/Asp equiv. Ratio | 80/20 | 75/25 | 66/34 | 50/50 | 33/67 | 25/75 |
| Calc. Product equiv. wt. (g/eq.) | 183 | 189 | 199 | 218 | 237 | 246 |
| Viscosity (mPa · s) @ 25° C. | 240 | 300 | 450 | 650 | 800 | 1,100 |

Analysis of some products by gas chromatography/mass spectrophotometry (GC/MS) showed the expected mixture of products, i.e., the bisaldimine of 4,4'-diamino-dicyclohexylmethane (A), the mixed aldimine/aspartate of 4,4'-diamino-dicyclohexylmethane (B), and the bisaspartate of 4,4'-diamino-dicyclohexylmethane (C). These results are listed in Table 1.1 as relative area %'s.

TABLE 1.1

|  | Bisaldimine (A) | Aldimine/aspartate (B) | Bisaspartate (C) |
| --- | --- | --- | --- |
| Example 1-A | 52% | 42% | 6% |
| Example 1-B | 43% | 47% | 8% |
| Example 1-C | 32% | 45% | 23% |

EXAMPLE 2

Mixed Aldimine/Aspartates Based on Other Aliphatic Diamines

2-Ethyl-1,5-pentanediamine (E-PDA, available from DuPont as DYTEK A) 4,4'-diamino-3,3'-dimethyl-dicyclohexylmethane (DM-HMDA, available from BASF as Laromin C 260), 1-amino-3,3,5-trimethyl-5-aminomethyl-cyclohexane (IPDA) were each used to prepare mixed aldimine/aspartates according to the invention. The diamine (exact charge amounts for all the components are listed in Table 2) was charged at ambient temperature to a 2 liter, three necked flask equipped with a stirrer, thermometer and an addition funnel. Maleic acid diethylester (DEM) was then added dropwise to the reaction pot with stirring at a rate such that the reaction exotherm did not increase the temperature of the reaction mixture above 50° C. Upon complete addition of the maleic acid diethyl ester, the contents of the reaction flask were maintained at 50° C. for a period of 6 hours. A slight excess of isobutyraldehyde (ca. 10% on a molar basis) was then added dropwise to the reaction mixture at a rate such that the reaction exotherm did not increase the temperature above 50° C. During the course of the reaction water was formed as a by-product as evidenced by the reaction mixture turning a milky white in appearance. Upon complete addition of the aldehyde, the reaction mixture was heated to maintain a temperature of 50° C. for a period of 1 hour. The water and excess isobutyraldehyde were removed by azeotropic distillation, followed by a vacuum (ca. 1 torr) stripping step to remove trace quantities of water.

TABLE 2

|  | G | H | I |
|---|---|---|---|
| Amine Type | E-PDA | DM-HMDA | IPDA |
| Amine (grams) | 116 | 238 | 170 |
| DEM (grams) | 172 | 172 | 172 |
| Amine/DEM Mol Ratio | 1.0/1.0 | 1.0/1.0 | 1.0/1.0 |
| Aldehyde (grams) | 85.5 | 85.5 | 85.5 |
| Mole of Aldehyde | 1.2 | 1.2 | 1.2 |
| Theo. Ald/Asp Equiv. Ratio | 50/50 | 50/50 | 50/50 |
| Products Equiv. Wt. (g/Equiv.) | 171 | 229 | 198 |
| Viscosity (mPa · s @ 25° C.) | 80 | 700 | 200 |

EXAMPLE 3 (Comparison)

Amine Co-Reactants Outside the Scope of the Present Invention

Various amounts of aldimine 1 (i.e., the bisaldimine of 4,4'-diamino-dicyclohexylmethane) were blended with aspartate 1 (PAE 1) at ambient temperature. The relative amounts and other data related to these co-reactants are presented in Table 3. These amine co-reactants are mixtures of only bisaldimines and bisaspartates, they do not contain the mixed aldimine/aspartates of the present invention.

TABLE 3

|  | J | K | L | M |
|---|---|---|---|---|
| Aldimine 1 (wt. %) | 70 | 63 | 53 | 37 |
| PAE 1 (wt. %) | 30 | 37 | 47 | 63 |
| Viscosity (mPa · s @ 25° C.) | 280 | 360 | 380 | 600 |
| Equiv. wt. (g/eq) | 183 | 189 | 199 | 218 |
| Aldimine/Aspartate Equiv. Ratio | 80/20 | 75/25 | 66/34 | 50/50 |

EXAMPLE 4

Coating Systems Containing Improved Compatibility Amines According to the Invention.

Ambient temperature-curing polyurea coating systems were prepared at 100% solids by combining the amine co-reactants listed in Table 4 with polyisocyanate 1 at an NCO/N equivalent ratio of 1:1. The amine co-reactants and polyisocyanates were mixed at ambient temperature and allowed to sit for 5 minutes before they were applied at a 5 mil wet film thickness (WFT) to a glass plate. All cured films exhibited excellent performance properties.

A particular co-reactant (listed in Table 4) was determined to be compatible or incompatible with polyisocyanate 1 by examining the appearance of the mixtures and films drawn down on glass panels at 5 mil WFT. Immiscibility and cloudiness were used as indicators of incompatibility. In Table 4 a "+" indicates that the polyisocyanate was compatible with the co-reactant, while a "–" indicates that the polyisocyanate was incompatible with the co-reactant.

Dry times of coating systems based on polyisocyanate 1 or 3 and the amine co-reactants were measured by preparing a 5 mil drawdown on glass and placing a 1 hour Gardner Drytime recorder on the film under ambient conditions. The Gardner dry time was determined using a Gardner Circular Drying Time Recorder.

Set-to-touch—During the first stage of drying the film is mobile and partially flows back into the scribed channel. The film may be considered "set-to-touch" when it no longer flows back and the stylus begins to leave a clear channel.

Hard-dry—when the stylus no longer ruptures the film, but moves freely upon the surface, the cross-section of the film may be considered to have reached the "hard-dry" condition.

The results are set forth in Table 4.

Viscosity measurements of the coating systems were carried out at ambient temperature 5 minutes after mixing the components and 65 minutes after mixing. The ratio of the viscosity at these times is designated $\eta_{65}/\eta_5$, which is an indicator of pot life. The higher the value of this ratio the shorter the pot life of the coating system. The results are summarized in Table 4.

TABLE 4

| Co-reactant | Compatibility | Pot Life | | | Gardner Dry Times | |
| --- | --- | --- | --- | --- | --- | --- |
| | | $\eta_5$(mPa · s) | $\eta_{65}$(mPa · s) | $\eta_{65}/\eta_5$ | set to touch | hard dry |
| | Iso 3 | | | | | |
| Ex. 1-A | + | 1,000 | 2,975 | 3.0 | 7 min. | 17 min. |
| Ex. 3-J (Comp) | + | 1,000 | 3,125 | 3.1 | 15 min. | 45 min. |
| | Iso 1/Iso 2[a] | | | | | |
| Ex. 1-A | –/– | NA[b] | NA[b] | NA[b] | NA[b] | NA[b] |
| Ex. 3-J (Comp) | –/– | NA[b] | NA[b] | NA[b] | NA[b] | NA[b] |
| Ex. 1-B | +/+ | 2,300 | 10,500 | 4.6 | 7 min. | 15 min. |
| Ex. 3-K (Comp) | –/– | 1,900 | 9,090 | 4.8 | 5 min. | 20 min. |
| Ex. 1-C | +/+ | 1,450 | 7,500 | 5.2 | 5 min. | 17 min. |
| Ex. 3-L (Comp) | +/– | 1,525 | 15,900 | 10.4 | 7 min. | 20 min. |
| Ex. 1-D | +/+ | 1,950 | 19,200 | 9.8 | 5 min. | 15 min. |
| Ex. 3-M (Comp) | +/+ | 3,000 | 50,000 | 16.7 | 7 min. | 25 min. |
| Aldimine 1 (Comp) | –/– | NA[b] | NA[b] | NA[b] | | |
| Aspartate 1 (Comp) | +/+ | 9,500 | gel | | 5 min. | 20 min. |

[a] = Pot lives and Gardner Dry Times determined from coating systems based on polyisocyanate 1;
[b] = Not available due to the coating mixture separating.

The above examples serve to illustrate the improved combination of compatibility, pot life, and dry times obtained when using the improved compatibility co-reactants according to the invention.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An aldimine/aspartate corresponding to the formula

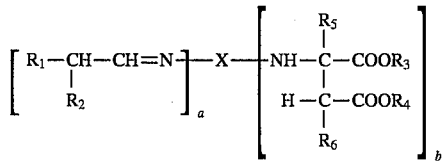

wherein

X represents an organic group which has a valency of n and is inert towards isocyanate groups at a temperature of 100° C. or less, $R_1$ and $R_2$ may be the same or different and represent optionally substituted hydrocarbon radicals, or $R_1$ and $R^2$ together with the β-carbon atom form a cycloaliphatic or heterocyclic ring and $R_3$ and $R_4$ may be identical or different and represent organic groups which are inert towards isocyanate groups at a temperature of 100° C. or less, $R_5$ and $R_6$ may be identical or different and represent hydrogen or organic groups which are inert towards isocyanate groups at a temperature of 100° C. or less, and a and b represent integers with a value of 1 to 5, provided that the sum of a and b is 2 to 6.

2. The aldimine/aspartate of claim 1 wherein $R_1$ and $R_2$ represent hydrocarbon radicals containing 1 to 6 carbon atoms, $R_3$ and $R_4$ represent a methyl or ethyl group, $R_5$ and $R_6$ represent hydrogen, a is 1 and b is 1.

3. The aldimine/aspartate of claim 1 wherein X corresponds to the radical obtained by removing the amino groups from bis-(4-aminocyclohexyl)-methane, $R_1$ represents a methyl group and $R_2$ represents an ethyl group.

4. The aldimine/aspartate of claim 2 wherein X corresponds to the radical obtained by removing the amino groups from bis-(4-aminocyclohexyl)-methane, $R_1$ represents a methyl group and $R_2$ represents an ethyl group.

* * * * *